(12) United States Patent
Selifonov (10) Patent No.: US 10,337,075 B2
(45) Date of Patent: Jul. 2, 2019

(54) PROCESS AND APPARATUS FOR TREATMENT OF BIOMASS

(71) Applicant: Sergey Alexandrovich Selifonov, Mountain View, CA (US)

(72) Inventor: Sergey Alexandrovich Selifonov, Mountain View, CA (US)

( * ) Notice: Subject to any disclaimer, the term of this patent is extended or adjusted under 35 U.S.C. 154(b) by 5 days.

(21) Appl. No.: 15/532,414

(22) PCT Filed: Dec. 2, 2015

(86) PCT No.: PCT/US2015/063531
§ 371 (c)(1),
(2) Date: Jun. 1, 2017

(87) PCT Pub. No.: WO2016/090046
PCT Pub. Date: Jun. 9, 2016

(65) Prior Publication Data
US 2017/0362671 A1 Dec. 21, 2017

Related U.S. Application Data

(60) Provisional application No. 62/194,463, filed on Jul. 20, 2015, provisional application No. 62/097,004,
(Continued)

(51) Int. Cl.
*C12M 1/00* (2006.01)
*C13K 13/00* (2006.01)
(Continued)

(52) U.S. Cl.
CPC ............ *C13K 13/002* (2013.01); *A23K 10/12* (2016.05); *A23K 10/32* (2016.05); *C12M 45/06* (2013.01);
(Continued)

(58) Field of Classification Search
CPC ....... Y02E 50/10; Y02E 50/343; C12M 45/06
See application file for complete search history.

(56) References Cited

U.S. PATENT DOCUMENTS

| 4,024,356 A | 5/1977 | Duimelaar |
| 4,272,383 A | 6/1981 | McGrew |
| 4,780,415 A | 10/1988 | Ducellier et al. |

FOREIGN PATENT DOCUMENTS

| DE | 2809531 A1 | 9/1978 |
| FR | 2994441 A1 | 2/2014 |

(Continued)

OTHER PUBLICATIONS

Machine translation of JP-2005205252-A (Year: 2005).*
(Continued)

*Primary Examiner* — Ellen M McAvoy
*Assistant Examiner* — Ming Cheung Po
(74) *Attorney, Agent, or Firm* — Dorsey & Whitney LLP (57) ABSTRACT

Reactor assemblies and methods for hydrolytic biomass conversion are disclosed herein. The reactor assemblies employ solely hydrostatic pressure, applied by the liquid biomass slurry, as means of providing pressure necessary to maintain high temperature conditions suitable for hydrolytic biomass conversion resulting in the formation of soluble pentose compounds. In embodiments, the methods employed in conjunction with the reactor assemblies yield soluble $C_5$ carbohydrates in the forms of oligosaccharides and monosaccharides from one or more biomass slurries.

6 Claims, 3 Drawing Sheets

Related U.S. Application Data filed on Dec. 26, 2014, provisional application No. 62/086,621, filed on Dec. 2, 2014, provisional application No. 62/086,615, filed on Dec. 2, 2014.

(51) Int. Cl.
| | | |
|---|---|---|
| *A23K 10/32* | (2016.01) | |
| *A23K 10/12* | (2016.01) | |
| *C12P 7/10* | (2006.01) | |
| *C12P 7/18* | (2006.01) | |

(52) U.S. Cl.
CPC ........ *C12P 7/10* (2013.01); *C12P 7/18* (2013.01); *Y02E 50/16* (2013.01); *Y02P 60/877* (2015.11)

(56) References Cited

FOREIGN PATENT DOCUMENTS

| | | | |
|---|---|---|---|
| JP | 2005205252 A | * | 8/2005 |
| WO | 2010061054 A1 | | 6/2010 |

OTHER PUBLICATIONS

International Search Report and Written Opinion dated Mar. 10, 2016 in connection with International Patent Application No. PCT/US2015/063531, 13 pages.

* cited by examiner

PROCESS AND APPARATUS FOR TREATMENT OF BIOMASS

CROSS-REFERENCE TO RELATED APPLICATIONS

This application is a national stage application of International Patent Application No. PCT/US2015/063531, filed Dec. 2, 2015, entitled "Process and Apparatus for Treatment of Biomass," which claims priority to U.S. Provisional Patent Application No. 62/086,621, filed Dec. 2, 2014, U.S. Provisional Patent Application No. 62/086,615, filed Dec. 2, 2014, U.S. Provisional Patent Application No. 62/097,004, filed Dec. 26, 2014, and U.S. Provisional Patent Application No. 62/194,463, filed Jul. 20, 2015, each of which is incorporated by reference herein, in the entirety and for all purposes.

TECHNICAL FIELD

Disclosed are methods and apparatuses for processing lignocellulosic biomass for the production of water-soluble pentose compounds ($C_5$ oligosaccharides and monosaccharides).

BACKGROUND

Inedible parts of various plant species used in agriculture and sylviculture worldwide are a valuable potential resource for renewable and sustainable production of many organic chemical compounds for industrial uses. Enabling effective industrial uses of the non-food biomass for such needs would also alleviate societal concerns associated with the current industrial practices of converting some food-grade agricultural crop ingredients into non-food industrial products.

The operational difficulty and high costs of separation of the chief polysaccharide ingredients of the cellulosic biomass into usable chemical compounds such as pentoses and hexoses is well documented. Primary methods for solubilization and separating of polysaccharides occurring in cellulosic biomass involve use of reagents such as mineral acids, alkali, organic solvents or other chemical compounds of considerable cost, thereby requiring recovery and recycling in the process. Use of corrosive materials such as mineral acids also requires costly corrosion-resistant equipment. Methods which rely on uses of enzymes for depolymerization of cellulosic and hemicellulosic polymers also remain quite inefficient and costly. While it is possible to separate some of carbohydrates from cellulosic biomass in soluble form without addition of mineral acids, alkali, sulfur dioxide, ammonia or other chemical additives, the conditions for effecting hydrolytic solubilization and/or depolymerization of polysaccharides of the cellulosic biomass require operating hydrolysis at high temperature and under high pressure conditions.

Apparatuses known in the art and capable of continuously moving biomass solids against high pressure of the heated hydrolysis containment is also vulnerable to rapid abrasive wear due to action of dust, sand, rocks and other mineral particles incidentally associated with biomass solids, such as silica in cereal straw or hulls.

SUMMARY

In embodiments, disclosed herein is a reactor assembly comprising: a hydrostatically pressurized hydrolysis zone comprising a discharge valve and heat source; an addition tube positioned above and in fluid communication with the hydrolysis zone and extending substantially vertically from the hydrolysis zone, the addition tube equipped with an addition port for ambient pressure application of biomass solids to an aqueous liquid at the top of the addition tube; and a biomass slurry comprising biomass and an aqueous liquid, the slurry contained within the hydrolysis zone and the addition tube; wherein the slurry at the top of the addition tube is maintained at ambient pressure and at a temperature equal or below the boiling temperature of the aqueous liquid at ambient pressure; wherein the temperature of the slurry in the hydrolysis zone is about 120° C. to 180° C.; wherein the hydrostatic pressure in the hydrolysis zone due to the height of the slurry in the addition tube is greater than the vapor pressure of the aqueous liquid contained in the hydrolysis zone; and wherein the reactor assembly is configured and adapted to produce a liquid hydrolysate comprising dissolved pentose compounds.

In embodiments, disclosed herein is a reactor assembly comprising: a hydrostatically pressurized hydrolysis zone comprising a discharge valve and heat input; an addition tube positioned above and in fluid communication with the hydrolysis zone and extending substantially vertically from the hydrolysis zone, the addition tube equipped with an addition port for ambient pressure application of biomass solids to an aqueous liquid at the top of the addition tube; and (c) an aqueous reaction medium comprising biomass; a discharge tube separate from the addition tube, the discharge tube positioned above and in fluid communication with the hydrolysis zone and extending substantially vertically from the hydrolysis zone; and a biomass slurry comprising biomass and an aqueous liquid, the slurry contained within the hydrolysis zone, the addition tube, and the discharge tube; wherein the slurry at the top of the addition tube is maintained at ambient pressure and at a temperature equal or below the boiling temperature of the aqueous liquid at ambient pressure; wherein the temperature of the slurry in the hydrolysis zone is about 120° C. to 180° C.; wherein the hydrostatic pressure in the hydrolysis zone due to the height of the slurry in the addition tube is greater than the vapor pressure of the aqueous liquid contained in the hydrolysis zone; and wherein the reactor assembly is configured and adapted to produce a liquid hydrolysate comprising dissolved pentose compounds.

In embodiments, disclosed herein is a reactor assembly comprising: a hydrostatically pressurized hydrolysis zone comprising a discharge valve and heat input; an addition tube positioned above and in fluid communication with the hydrolysis zone and extending substantially vertically from the hydrolysis zone, the addition tube equipped with an addition port for ambient pressure application of biomass solids to an aqueous liquid at the top of the addition tube; and (c) an aqueous reaction medium comprising biomass; a discharge tube positioned above and in fluid communication with the hydrolysis zone and extending substantially vertically from the hydrolysis zone, wherein a portion of the addition tube is enclosed within the discharge tube, wherein a biomass slurry the aqueous reaction medium in the discharge tube is in the contact with the wall of the addition tube; and a biomass slurry comprising biomass and an aqueous liquid, the slurry contained within the hydrolysis zone, the addition tube, and the discharge tube such that the slurry in the discharge tube contacts an outer wall of the addition tube; wherein the slurry at the top of the addition tube is maintained at ambient pressure and at a temperature equal or below the boiling temperature of the aqueous liquid at ambient pressure; wherein the temperature of the slurry in the hydrolysis zone is about 120° C. to 180° C.; wherein the hydrostatic pressure in the hydrolysis zone due to the height of the slurry in the addition tube is greater than the vapor pressure of the aqueous liquid contained in the hydrolysis zone; and wherein the reactor assembly is configured and adapted to produce a liquid hydrolysate comprising dissolved pentose compounds.

In embodiments, disclosed herein is process for making soluble pentose compounds from biomass comprising pentose polymers in a reactor assembly, the process comprising: forming a biomass slurry in a biomass mixing zone of the reactor assembly at an atmospheric pressure by mixing biomass with an aqueous liquid, wherein the temperature of the aqueous liquid in the slurry is maintained at or below the boiling point thereof at atmospheric pressure; transferring the slurry downward from the mixing zone to a hydrostatically pressurized hydrolysis zone by a gravity flow through an addition tube, the addition tube providing a continuous liquid contact between the mixing zone and a hydrolysis zone at the bottom of the addition tube, wherein the transfer of the slurry is provided by the hydrostatic pressure due to the height of the slurry in the addition zone that exceeds the hydrostatic pressure provided by the remainder of the slurry contained in the reactor assembly; heating the slurry to achieve and maintain an operational temperature of about 120° C. to 180° C. in the hydrostatically pressurized hydrolysis zone; maintaining a slurry level in the addition zone to provide a hydrostatic pressure in the hydrolysis zone in excess of the vapor pressure of the aqueous liquid at the operational temperature of the hydrolysis zone, withdrawing slurry though a discharge valve connected to the hydrolysis zone, or from above the hydrolysis zone via a discharge tube connected to the hydrolysis zone, wherein entry of slurry to the discharge valve or discharge tube takes place at a positive hydrostatic pressure of the slurry or at atmospheric pressure, thereby providing a hydrolyzed biomass slurry comprising biomass solids and a liquid hydrolysate, the hydrolyzed biomass slurry having reduced content of pentosanes and the liquid hydrolysate having increased content of soluble pentose compounds, as compared to the composition of biomass and aqueous liquid in the slurry formed in the mixing zone. In some examples, the process may further involve separating the hydrolyzed biomass solids from the liquid hydrolysate. In some embodiments, a portion of separated liquid hydrolysate may be mixed with fresh biomass in the mixing zone or with biomass slurry in the addition tube. In some examples, the hydrolyzed biomass solids may be subjected to an aqueous washing step, wherein the liquid resulting from the washing step is mixed with biomass in the biomass mixing zone or is added to the addition tube. In some embodiments, the biomass slurry entering the hydrolysis zone may comprise about 4 wt % to 12 wt % soluble pentose compounds. In some examples, the pH of the aqueous liquid in the hydrolysis zone may be about 2 to 4.8, as measured at 25° C. In some embodiments, the liquid hydrolysate may be further treated with yeast, wherein the treatment with yeast results in one or more effects on the composition of the liquid hydrolysate, said effects selected from a group of consisting of: (a) removal of soluble hexose compounds, (b) reduction of xylose to xylitol, or (c) production of ethanol.

Additional advantages and novel features of the invention will be set forth in part in the description that follows, and in part will become apparent to those skilled in the art upon examination of the following, or may be learned through routine experimentation upon practice of the invention. It will be understood that each and every embodiment of the reactor assemblies and methods described herein are intended to be used in conjunction with each and every variation and limitation thereof described elsewhere herein and without limitation as to the number of variations or limitations incorporated in a recited embodiment unless a variation or limitation is expressly excluded. Further, it will be understood that in each and every embodiment recited herein, the reactor assemblies and methods suitably comprise, consist essentially of, or consist of the recited components or steps.

DETAILED DESCRIPTION

Definitions

Unless otherwise defined, all technical and scientific terms used herein have the same meaning as commonly understood by one of ordinary skill in the art. In case of conflict, the present document, including definitions, will control. Preferred methods and apparatuses are described below, although methods and apparatuses similar or equivalent to those described herein can be used in practice or testing of the present invention. All publications, patent applications, patents and other references mentioned herein are incorporated by reference in their entirety and for all purposes. The materials, methods, apparatuses, and examples disclosed herein are illustrative only and not intended to be limiting.

As used herein, the term "biomass" means lignocellulosic biomass, that is, a biological solid that at least initially (prior to being subjected to the methods of the invention) includes cellulose and lignin. The biomass is derived from one or more plant sources and contains variable amounts of polymers comprising pentose polysaccharides. In embodiments, the biomass is not a food source for humans.

As used herein, the term "slurry" or "biomass slurry" means a combination of biomass and an aqueous liquid. The slurry includes at least about 1 wt % biomass solids and as much as about 50 wt % biomass solids; in embodiments the slurry includes about 5 wt % to 25 wt % biomass solids or about 10 wt % to 15 wt % biomass solids.

As used herein, the term "aqueous liquid" means water or a combination of water and a water-miscible solvent. The aqueous liquid comprises, consists essentially of, or consists of water. In embodiments, the aqueous liquid includes one or more soluble products of biomass hydrolysis and/or solvation.

As used herein, the term "pentose" or "pentose compounds" mean a genus of compounds comprising (i) xylose (ii) arabinose (iii) ribose, (iv) di- and oligo-saccharides thereof, their polymeric forms (pentosane), and (v) any oligo- or polysaccharides that are a combination of pentose glycoside units and hexose glycoside units. The definition includes single species, esterified versions of these compounds incorporating acetic acid or another carboxylic acid, and mixtures thereof. The presence of soluble pentose compounds in any aqueous liquid can be established by a general laboratory method known in the art for determining pentoses by means of converting pentosane compounds to furfural via hydrochloric acid decomposition of pentoses and by measuring amounts of furfural formed.

As used herein, the term "pentosane" or "pentosane-containing biomass" means the organic matter of plant, algal or microbial origin having a total pentose content in excess of 2 weight percent of the dry organic matter, as measured by release of furfural via the hydrochloric acid decomposition method for determining pentose content.

As used herein, relative terms such as "downward", "upward", "top", "bottom" and the like are defined from the standpoint of a human standing upright on the ground proximal to a reactor assembly of the invention. Terms such as "vertical", "horizontal", and the like are used to describe reactor assemblies and methods of the invention relative to the ground proximal to the reactor assembly.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, pressure, partition coefficient, rate, solubility, temperature, and the like; intended values include thickness, yield, weight, concentration, and the like. The effect on methods that are modified by "substantially" include the effects caused by variations in type or amount of materials used in a process, variability in machine settings, the effects of ambient conditions on a process, and the like wherein the manner or degree of the effect does not negate one or more intended properties or results; and like proximate considerations. The effect on apparatuses that are modified by "substantially" include minor or inadvertent variations in apparatus tolerances, dimensions, or settings, variations in measurement or readout by components employed to control conditions within the apparatus, and the like. Where modified by the term "substantially" the claims appended hereto include equivalents to these types and amounts of materials.

Discussion

Disclosed are methods and reactor assemblies for dissolving and separating pentose compounds from biomass comprising cellulose and lignin (lignocellulosic biomass).

The reactor assemblies of the invention employ hydrostatic pressure to maintain conditions suitable for hydrolytic biomass conversion. In embodiments, the methods employed in conjunction with the reactor assemblies yield soluble $C_5$ carbohydrates in the forms of oligosaccharides and monosaccharides from one or more biomass slurries applied to a reactor assembly. In some embodiments, the reactor assemblies of the invention rely solely on hydrostatic pressure as means of providing pressure necessary to maintain high temperature conditions suitable for hydrolytic biomass conversion resulting in the formation of soluble pentose compounds.

The reactor assemblies enable ambient pressure addition of biomass solids to the reactor assembly and mixing thereof with a liquid, thereby obviating the need for reactor components having pressure locks capable of moving solids against the pressure within the reactor assembly. The methods of the invention require no added organic solvents, acids, bases, sulfur dioxide, oxidants, ammonia or enzyme reactants. Employing conditions consistent with the methods of the invention, the reactor assemblies rely on acidity of organic acids, such as acetic acid, released from the biomass during the process. The product of the system is a hydrolysate comprising water-soluble pentose compounds ($C_5$ mono- and/or oligosaccharides).

The combination of pressure and temperature conditions necessary for successful hydrolytic solubilization of pentose compounds from cellulosic biomass, in embodiments without addition of exogenous enzymes, mineral acids, alkali or other chemical additives, is effectively achieved by the reactor assemblies of the invention when used in conjunction with the methods of the invention. The reactor assemblies include a hydrolysis zone wherein the pressure necessary to maintain an aqueous slurry therein in a substantially non-boiling state is provided solely by means of hydrostatic pressure. The hydrostatic pressure is applied by application of the aqueous slurry via an addition tube. The addition tube is situated substantially vertically in relation to the hydrolysis zone and is in liquid communication with the hydrolysis zone at a proximal end thereof. The addition tube proceeds upwardly away from the hydrolysis zone, further wherein the addition tube includes an opening distal from the hydrolysis zone to receive the aqueous slurry. The addition tube thereby achieves two important functions in the reactor assemblies: conveyance of an aqueous slurry toward the hydrolysis zone; and application of hydrostatic pressure to the hydrolysis zone by virtue of the mass of the slurry moving through the addition tube toward the hydrolysis zone.

Thus, in embodiments, during operation of the reactor assembly a biomass slurry is applied at ambient pressure to the top of the addition tube. As the addition tube is filled, hydrostatic pressure is applied to the hydrolysis zone without any pressure-locking or pressure-inducing devices such as pumps, feeder screws, augers, or other pressurized conveyors. An opening of the addition tube distal to the hydrolysis zone is operable to apply slurry to the addition tube. In some embodiments a mixing zone situated at the distal end of the addition tube is operable as a mixing zone for forming a slurry from biomass solids and an aqueous liquid applied separately to the mixing zone. Gravitationally facilitated movement of slurry proceeds in an overall vertical and downward direction through the addition tube to provide a supply of the slurry to the hydrolysis zone. The residence time in the hydrolysis zone is controlled by the volume of the hydrolysis zone relative to the volume of the addition channel and the rate of applying slurry to the addition tube. Spent, or hydrolyzed, biomass solids are removed via a valve at the bottom of the hydrolysis zone or elsewhere, as will be described in detail below.

Reactor Assemblies

The reactor assemblies of the invention will now be described in detail by reference to FIGS. 1-3, wherein like reference numerals represent like components and assemblies throughout the several views. Reference to various embodiments, components, and assemblies does not limit the scope of the claims attached hereto.

Figure 1:
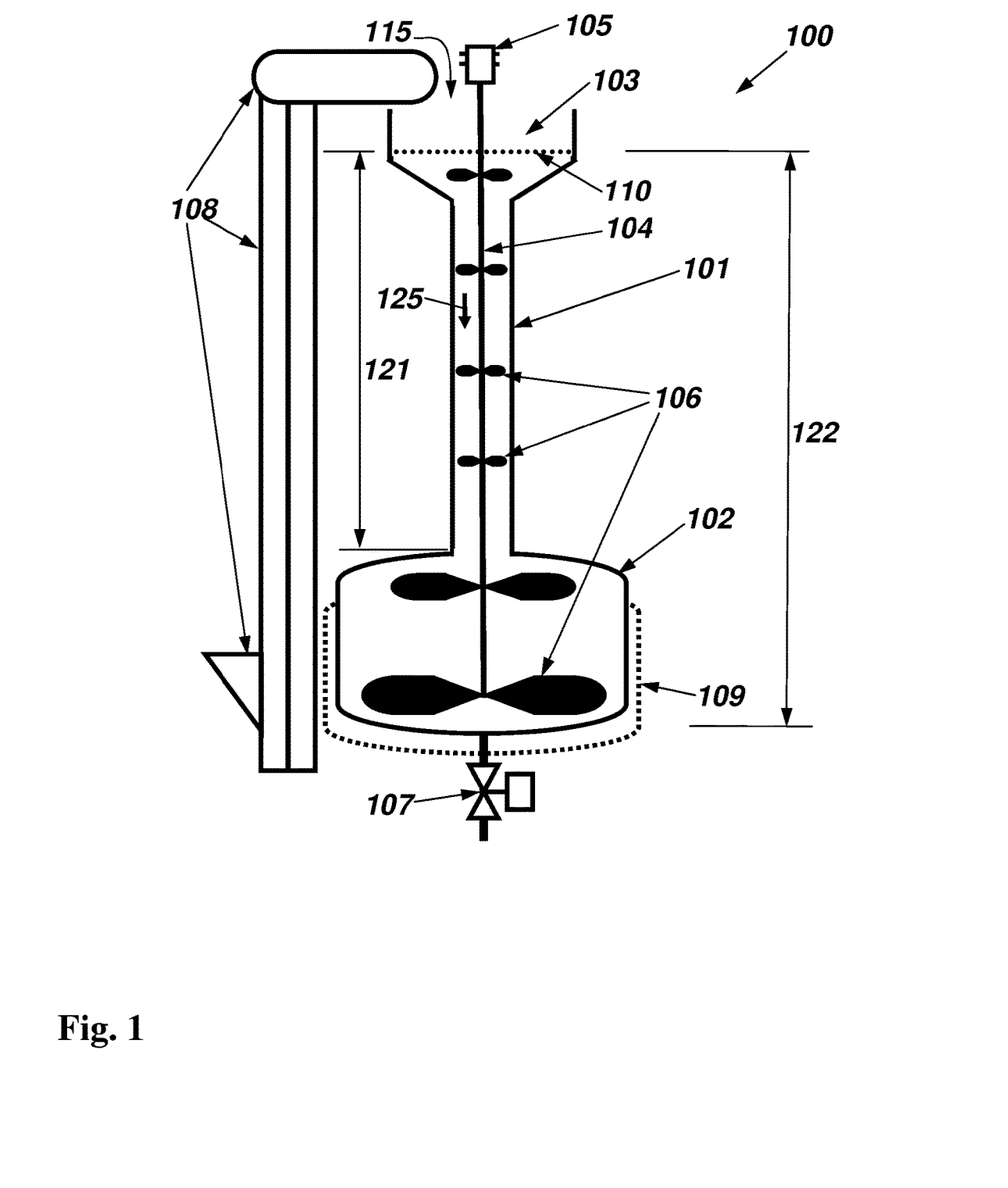
FIG. 1 is a schematic view of one reactor assembly of the invention.
Figure 2:
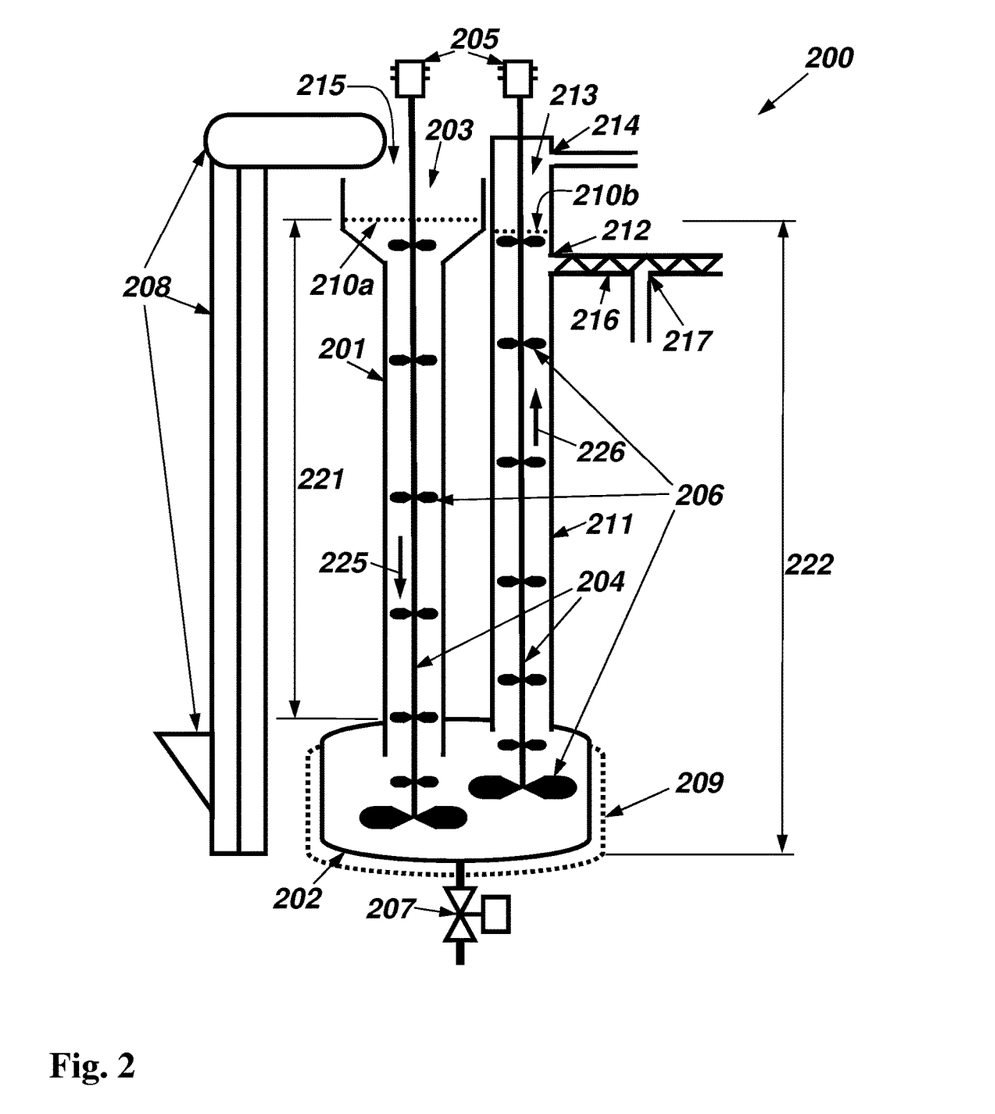
FIG. 2 is a schematic view of another reactor assembly of the invention.
Figure 3:
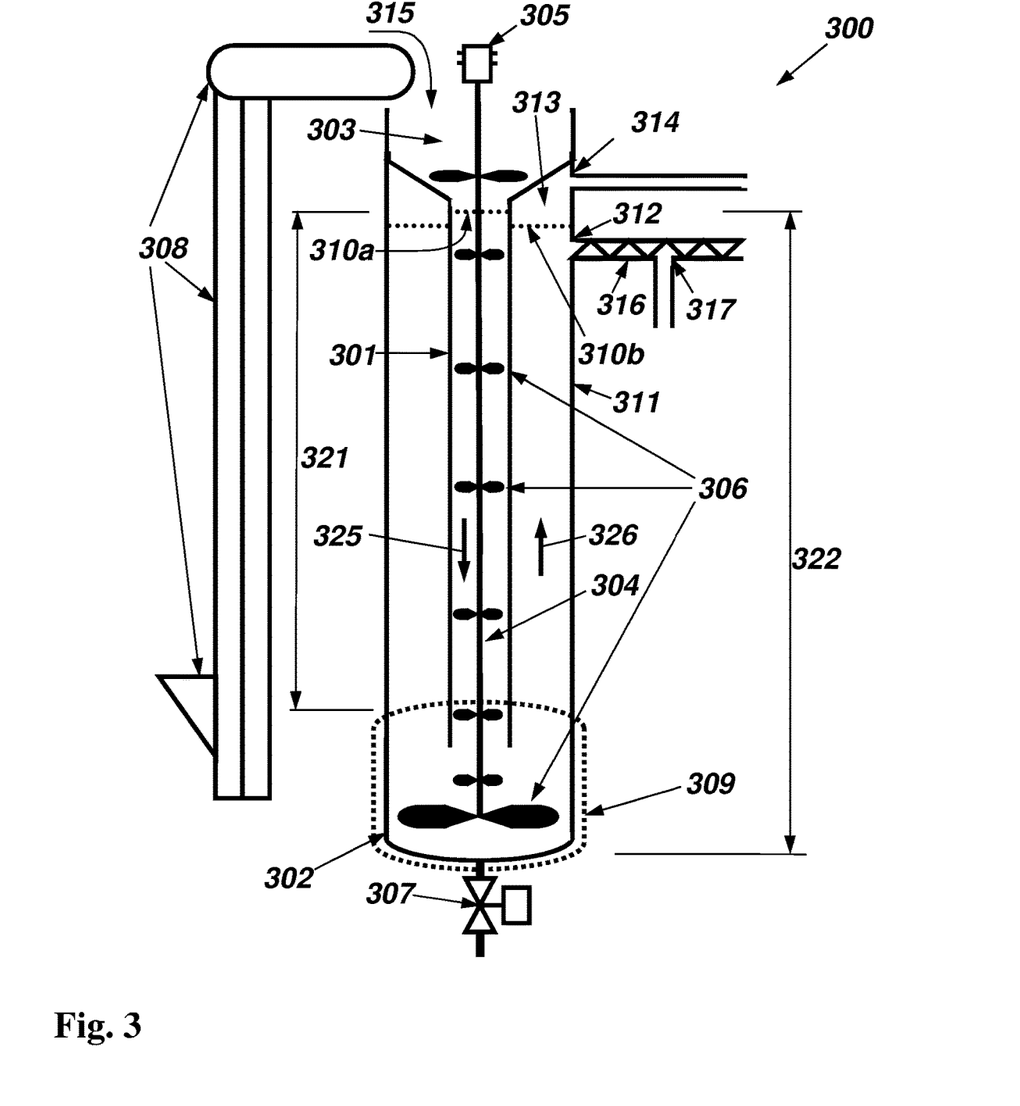
FIG. 3 is a schematic view of another reactor assembly of the invention.

Table 1 shows components corresponding to reactor assemblies schematically depicted as reactor assembly 100 of FIG. 1, reactor assembly 200 of FIG. 2, and reactor assembly 300 of FIG. 3.

TABLE 1

Components corresponding to reactor assemblies 100 (FIG. 1), 200 (FIG. 2), and 300 (FIG. 3).

| | Component Description |
|---|---|
| Reactor assembly 100 Component | |
| 101 | Addition tube |
| 102 | Hydrolysis zone |
| 103 | Mixing zone |
| 104 | Mixer shaft |
| 105 | Mixer motor |
| 106 | Mixer blades |
| 107 | Discharge valve |
| 108 | Bucket elevator |
| 109 | Heat exchanger jacket |
| 110 | Liquid level |
| 115 | Addition port |
| 121 | Height of liquid column in addition tube |
| 122 | Total height of liquid column in reactor assembly |
| 125 | Direction of flow in addition tube |
| Reactor assembly 200 Component | |
| 201 | Addition tube |
| 202 | Hydrolysis zone |
| 203 | Mixing zone |
| 204 | Mixer shaft |
| 205 | Mixer motors |
| 206 | Mixer blades |
| 207 | Discharge valve |
| 208 | Bucket elevator |
| 209 | Heat exchanger jacket |
| 210a | Liquid level in addition tube |
| 210b | Liquid level in discharge tube |
| 211 | Discharge tube |
| 212 | Discharge tube outlet |
| 213 | Discharge tube headspace |
| 214 | Steam outlet |
| 215 | Addition port |
| 216 | Dewatering module |
| 217 | Hydrolysate outlet |
| 221 | Height of liquid column in addition tube |
| 222 | Total height of liquid column in reactor assembly |
| 225 | Direction of flow in addition tube |
| 226 | Direction of flow in discharge tube |
| Reactor assembly 300 Component | |
| 301 | Addition tube |
| 302 | Hydrolysis zone |
| 303 | Mixing zone |
| 304 | Mixer shaft |
| 305 | Mixer motor |
| 306 | Mixer blades |
| 307 | Discharge valve |
| 308 | Bucket elevator |
| 309 | Heat exchanger jacket |
| 310a | Addition tube liquid level |
| 310b | Discharge tube liquid level |
| 311 | Discharge tube |
| 312 | Discharge tube outlet |
| 313 | Discharge tube headspace |
| 314 | Steam outlet |
| 315 | Addition port |
| 316 | Dewatering module |
| 317 | Hydrolysate outlet |
| 321 | Height of liquid column in addition tube |
| 322 | Total height of liquid column in reactor assembly |
| 325 | Direction of flow in addition tube |
| 326 | Direction of flow in discharge tube |

FIG. 1 is a schematic view of an embodiment 100 of a reactor assembly of the invention. Addition tube 101 is positioned substantially vertically and in fluid communication with hydrolysis zone 102, extending vertically upward and away from zone 102. At the top of addition tube 101 is mixing zone 103. Mixing zone 103 includes addition port 115 for applying biomass solids to addition tube 101. Optionally mixing zone 103 includes a widened portion, substantially as shown, to facilitate adding, mixing, or both. In some embodiments, biomass solids and an aqueous liquid are added contemporaneously to mixing zone 103. In other embodiments, a biomass slurry is added directly to addition port 115. Optionally, a mixer shaft 104 having mixer blades 106 is disposed vertically within addition tube 101 and operably connected to mixer motor 105. Motor 105 rotates mixer shaft 104 during operation of reactor assembly 100, which provides mixing of the addition tube contents by the rotating action of mixer blades 106 during the downward overall movement of slurry toward the hydrolysis zone 102. Rotating mixer blades 106 facilitate a more uniform distribution of solids and maintains downward movement of the slurry though addition tube 101.

A combination of biomass solids and water or an aqueous liquid is applied to addition tube 101 in an amount to maintain liquid level 110. Liquid level 110 is selected by the user to provide a targeted hydrostatic pressure to hydrolysis zone 102 during continuous or periodic operation of reactor assembly 100. The liquid level 110 is the same as, or is less than, the maximum height of the liquid column in addition tube 121. Total height of the liquid column in the reactor assembly is limited to height 122.

During operation of reactor assembly 100, biomass solids are delivered by bucket elevator 108 or by one or more other devices known in the art for conveyance, lifting and unloading agricultural products such as grains or mining materials at the appropriate height. The biomass is delivered to mixing zone 103 via addition port 115. A slurry is formed by further applying water or an aqueous liquid to mixing zone 103, via addition port 115 or another port to mixing zone 103 (not shown). The biomass and the water or aqueous liquid is mixed in mixing zone 103 and applied to addition tube 101 at distal (top) end thereof. The applied slurry proceeds downward 125 through addition tube 101 toward hydrolysis zone 102. In some embodiments, movement of the slurry is regulated, modifed, mediated, or otherwise affected by movement of mixer blades 106. The slurry is received in hydrolysis zone 102 from the opening at proximal (bottom) end of addition tube 101. Heat is applied to the slurry disposed within hydrolysis zone 102 via heat exchanger jacket 109. The combination of water, heat, and pressure within hydrolysis zone 102 causes biomass hydrolysis, solvolysis, or a combination thereof (collectively referred to herein as hydrolysis). After a selected period of hydrolysis, hydrolyzed biomass is removed through discharge valve 107.

The materials employed to make the hydrolysis vessel 102 and discharge valve 107 is rated to withstand the hydrostatic pressure applied thereto by the total liquid column with height 122. The reactor body is heated by means of optional heat exchanger jacket 109. Heating is optionally and suitably provided by steam injections through steam injection ports located on the hydrolysis vessel 102 (not shown), and/or elsewhere on reactor assembly 100 as determined by one of skill. Elevation of the biomass solids to mixing zone 103 is accomplished, as shown in the exemplary embodiment of FIG. 1, by bucket elevator 108.

Mixing zone 103 is operable at or near atmospheric or ambient pressure to deliver one or more biomass slurries to the hydrolysis zone 102. In embodiments, hydrolysis of biomass and dissolution of pentose compounds therein is effected in hydrolysis zone 102 by heating the contents. The hydrostatic pressure present within hydrolysis zone 102 is sufficient to suppress boiling of the aqueous liquid therein at temperatures in excess of about 100° C., thereby providing conditions necessary for satisfactory biomass hydrolysis and accompanying dissolution of pentose compounds.

After a period of residence in the hydrolysis zone 102, the biomass slurry is converted to hydrolyzed biomass slurry. The hydrolyzed biomass slurry is discharged from hydrolysis zone 102 by opening discharge valve 107 or another such means of discharge situated substantially at the bottom of hydrolysis zone 102. The discharged hydrolyzed biomass slurry is applied to a vessel permitting eventual decrease in pressure to atmospheric or ambient values, and release of any steam or condensate associated with such pressure reduction. The hydrolyzed biomass slurry is then subjected further to one or more separations to separate the hydrolyzed biomass slurry into hydrolyzed biomass solids and liquid hydrolysate. Separation of solid biomass from liquid hydrolysate is suitably achieved using methods and apparatuses known in the art, for example dewatering screw presses, drum filters, filtration presses, hydrocyclones, centrifuges, passive sedimentation, or a combination of two or more thereof.

In some embodiments, after separation of the hydrolyzed biomass slurry into hydrolyzed biomass solids and liquid hydrolysate, a first portion of the hydrolysate is collected from discharge valve 107 for concentration thereof and for removal of intrinsic quantities of acetic acid by evaporation, using one or more evaporators known in the art, to result in a concentrated hydrolysate. The first portion in some embodiments is the entirety of the hydrolysate. The hydrolysate includes pentose compounds and other compounds soluble in the aqueous liquid. Optionally, in some embodiments a second portion of the hydrolysate is recycled e.g. by urging the hydrolysate second portion towards and into mixing zone 103, for example using a pump mechanism. Optionally, the hydrolyzed biomass solids are further subjected to one or more biomass washing steps to increase recovery of the dissolved or soluble pentose compounds from the hydrolyzed biomass solids.

FIG. 2 is a schematic view of another embodiment 200 of a reactor assembly of the invention. The principles of applying biomass slurry to create hydrostatic pressure for hydrolysis of the biomass are the same as described for reactor assembly 100. The reactor assembly 200 includes mixing zone 203 fluidly connected to addition tube 201 which is in turn fluidly connected to hydrolysis zone 202. However, reactor assembly 200 includes discharge tube 211 fluidly connected to hydrolysis zone 202. The biomass slurry is applied to addition tube 201 and proceeds in direction 225 toward hydrolysis zone 202 in similar fashion to the applying described above. The biomass hydrolysis occurs in hydrolysis zone 202 in the same manner as described above. After a period of residence, a hydrolyzed biomass slurry is obtained; the hydrolyzed biomass slurry exits hydrolysis zone 202 by proceeding in direction 226 through discharge tube 221 and eventually reaching discharge tube outlet 212 where the hydrolyzed biomass slurry then proceeds toward dewatering module 216.

A combination of biomass solids and water or an aqueous liquid is applied to addition tube 201 in an amount to maintain liquid level 210a. Liquid level 210a is selected by the user to provide a targeted hydrostatic pressure to hydrolysis zone 202 during continuous or periodic operation of reactor assembly 200. The liquid level 210a is the same as, or is less than, the maximum height of the liquid column in addition tube 221. Total height of the liquid column in the reactor assembly 200 is limited to height 222.

Discharge tube 211 facilitates periodic or continuous discharge of hydrolyzed biomass slurry from reactor assembly 200. Liquid level 210b in discharge tube 211 is selected by the user. In some embodiments liquid level 210b is selected to be below liquid level 210a in addition tube 201 due to hydrodynamic resistance of the flow of the biomass slurry through the reactor assembly 200. In other embodiments liquid level 210b is variable and fluctuates with the flow of liquid within reactor assembly 200 or with the rate of discharge of hydrolyzed biomass slurry through discharge tube outlet 212. From discharge tube outlet 212, the hydrolyzed biomass slurry proceeds toward and into dewatering module 216. Dewatering module 216 includes one or more dewatering apparatuses known in the art to separate particulate solids from liquids, for example dewatering screw presses, drum filters, filtration presses, hydrocyclones, centrifuges, passive sedimentation, or a combination of two or more thereof.

In embodiments, discharge valve 207 is engaged to remove sediment such as sand, clay or other incidental heavier-than-water debris from the bottom area of hydrolysis vessel 202, thereby decreasing risk of damage or excessive wear to biomass dewatering equipment 216. The reactor assembly comprises optional mixing devices exemplified by depicted blades or paddles 206, attached to a mixer shaft 204 and propelled by a motor 205. Such devices facilitate flow of the biomass slurry through the addition 201 and/or discharge 211 channels, as well as mixing of the slurry in the hydrolysis zone of the vessel 202.

Any residual pressure in excess of atmospheric/ambient pressure in discharge tube headspace 213 is relieved to eventual atmospheric pressure via steam outlet 214 with optional heat recovery therefrom by means of a heat exchanger (not shown). Steam outlet 214 is optional, or in some embodiments is optionally fully closed, thereby giving rise to pressure excess of ambient/atmospheric within discharge tube headspace 213. In such embodiments, the movement of hydrolyzed biomass slurry is facilitated by hydrostatic pressure due to differences between the liquid level 210a and the height at which discharge tube outlet 212 is positioned. One or more discharge tube outlets, exemplified by outlet 212, are suitably connected to one or more dewatering modules 216; outlets 212 are suitably located at any height of the discharge tube 211 with ascending flow 226.

For many hydrolyzed biomass slurries, a hydrostatic pressure of about 0.3 to 1.5 bar is sufficient to allow for effective movement of the slurry into and through a dewatering module 216. The rate of advancement of the hydrolyzed biomass slurry through dewatering module 216 determines the overall flow rate of the slurry through addition tube 201, hydrolysis zone 202, and discharge tube 211. Within the dewatering module 216, hydrolyzed biomass slurry is subjected to a separation into hydrolyzed biomass solids and liquid hydrolysate. The liquid hydrolysate exits the dewatering module 216 via hydrolysate outlet 217. A first portion or all of the liquid hydrolysate is withdrawn for concentration of pentose compounds and other soluble compounds, similarly to the above described concentration process. A second portion of the liquid hydrolysate is optionally recycled by reapplying to reactor assembly 200, similarly to hydrolysate recycling described for reactor assembly 100.

FIG. 3 is a schematic view of another embodiment of a reactor assembly 300 of the invention. The reactor assembly 300 includes addition tube 301, hydrolysis zone 302, and discharge tube 311 that function similarly to300 addition tube 201, hydrolysis zone 202, and discharge tube 211 of FIG. 2 except that addition tube 301 is enclosed within discharge tube 311. That is, discharge tube 311 surrounds addition tube 301. In some embodiments both addition tube 301 and discharge tube 311 are circular in cross section, wherein addition tube 301 is substantially centered and concentric within discharge tube 311 as shown in reactor assembly 300. Thus, biomass slurry applied to addition tube 301 with descending flow 325 is disposed within discharge tube 311 having ascending flow 326 of hydrolyzed biomass slurry.

In an alternative embodiment to the reactor assembly 300, slurry discharge tube 311 is enclosed within addition tube 301. In such embodiments, discharge tube 311 with hydrolyzed biomass slurry ascending flow 326 is disposed within addition tube 301 having descending flow 325 of biomass slurry applied at addition tube 301. In various alternative embodiments, the dimensions of hydrolysis zone 302 are wider, narrower, or the same as a width or diameter of the discharge tube 311 in the reactor assembly 300 in the embodiment shown in FIG. 3.

Liquid level 310b in discharge tube 311 is selected by the user. In some embodiments liquid level 310b is selected to be below liquid level 310a in addition tube 301 due to hydrodynamic resistance of the flow of the biomass slurry through the reactor assembly 300. In other embodiments liquid level 310b is variable and fluctuates with the flow of liquid within reactor assembly 300 or with the rate of discharge of hydrolyzed biomass slurry through discharge tube outlet 312. From discharge tube outlet 312, the hydrolyzed biomass slurry proceeds toward and into dewatering module 316. For many hydrolyzed biomass slurries, a hydrostatic pressure of about 0.3 to 1.5 bar is sufficient to allow for effective movement of the hydrolyzed biomass slurry into and through a dewatering module 316 via discharge tube outlet 312.

Any residual pressure in excess of atmospheric/ambient pressure in discharge tube headspace 313 is relieved to eventual atmospheric pressure via steam outlet 314 with optional heat recovery therefrom by means of a heat exchanger (not shown). Steam outlet 314 is optional, or in some embodiments is optionally fully closed, thereby giving rise to pressure excess of ambient/atmospheric within discharge tube headspace 313. In such embodiments, the movement of hydrolyzed biomass slurry is facilitated by hydrostatic pressure due to differences between the liquid level 310a and the height at which discharge tube outlet 312 is positioned. One or more discharge tube outlets, exemplified by outlet 312, are suitably connected to one or more dewatering modules 316; outlets 312 are suitably located at any height of the discharge tube 311 with ascending flow 326.

In embodiments, discharge valve 307 is engaged to remove sediment such as sand, clay or other incidental heavier-than-water debris from the bottom area of hydrolysis zone 302 in similar fashion to discharge valve 207.

The reactor assemblies of FIGS. 1-3 are operated under conditions of temperature and pressure such that $C_5$ carbohydrates, including monosaccharide and oligosaccharide materials, are suitably dissolved in the liquid phase of the slurry. Operating pressure in the reactor assemblies are obtained through the use of hydrostatic pressure from the height of the liquid in the addition tube. No other source of pressure is required. Additionally, it is an advantage of the methods of the invention that an acid component, typically acetic acid, is self-generated during the hydrolysis; thus, no added acids, bases, or exogenous enzyme is required to produce high yields of pentoses within the obtained liquid hydrolysate.

The reactor assemblies of the invention are designed and assembled using materials and designs suitable for contact with aqueous biomass slurries at pH of 6 or less, further as subjected to hydrolysis materials and conditions as applicable. For example, the hydrolysis zone portion of a reactor assembly is made from materials and provided in a configuration suitable to withstand the presence of the slurry under pressurized conditions and at temperatures as high as about 180° C. In embodiments a metal or metal alloy such stainless steel or carbon steel, glass, certain engineering thermoplastics and thermosets, and the like are employed to form one or more portions of the reactor assemblies of the invention.

For practical convenience of operation and maintenance, the reactor assemblies are designed to reduce or avoid clogging by biomass particulates and pieces, and further to allow for cleaning and service of interior surfaces and equipment parts and sensors placed therein to monitor temperature, pressure, and the like. For practical convenience of fabrication, in some embodiments the addition tube, mixing zone, hydrolysis zone, or other portions of the reactor assembly have substantially circular cross sections. However, the reactor assembly is not so limited, and various portions thereof suitably have rectangular, oblong, hexagonal, etc. cross sections as determined by design.

In embodiments, an addition tube with a round cross section has an inner diameter of about 0.1 meter to 5 meters, or about 0.2 meter to 5 meters, or about 0.3 meter to 5 meters, or about 0.4 meter to 5 meters, or about 0.5 meter to 5 meters, or about 1 meter to 5 meters, or about 2 meters to 5 meters, or about 3 meters to 5 meters, or about 0.1 meter to 4 meters, or about 0.1 meter to 3 meters, or about 0.1 meter to 2 meters, or about 0.1 meter to 1 meter, or about 0.5 meter to 3 meters, or about 0.5 meter to 2 meters. Reactor assemblies resulting in large working volumes carry high construction costs and demand costly consolidation of large quantities of biomass. The same considerations for inner diameter of the biomass addition tube applies to the selected diameter of the discharge tubes as described above and other components of the reactor assemblies of the invention.

The addition tube of a reactor assembly has a sufficient height such that the addition tube substantially filled with biomass slurry provides a liquid column height necessary to provide the desired conditions of hydrostatic pressure within the hydrolysis zone. For example, if hydrolysis zone is intended to operate at about 160° C., then where the aqueous liquid consists essentially of or consists of water, a hydrostatic pressure of about 5.17 bar is required to maintain the aqueous liquid in the hydrolysis zone without boiling. In such embodiments, to achieve such hydrostatic pressure in the hydrolysis zone the minimum height (121 in FIG. 1, 221 in FIG. 2, 321 in FIG. 3) of a liquid column is about 52.7 meters. Many configurations are achieved by using the principle of applying a mass of biomass slurry above and in fluid communication with the hydrolysis zone, wherein the height of the liquid column is sufficient to apply a hydrostatic pressure within the hydrolysis zone suitable for maintaining a biomass slurry at a temperature above 100° C. an as high as 180° C. without boiling. In embodiments, the minimum height of the liquid column in the addition tube needed to maintain a non-boiling state in the hydrolysis zone can be decreased or increased according to the liquid column height necessary to apply a hydrostatic pressure equal to or in excess of the pressure of the saturated steam at the selected hydrolysis zone temperature.

In practice, the addition tube is constructed to contain liquid height in excess of the minimal value to accommodate for liquid level fluctuations, and to accommodate space requirements for mixing incoming biomass solids with aqueous liquid to form the biomass slurry. In part for this reason, it is advantageous in some embodiments to provide a mixing zone fluidly connected to the opening of the addition tube distal to the hydrolysis zone. In embodiments the mixing zone is simply a widened portion of the addition tube. In some embodiments, the mixing zone further includes an addition port designed and adapted for delivery of biomass to the mixing zone from the conveyance means employed to lift and unload the biomass.

It will be understood by those of skill that ambient pressure is subject to fluctuations from atmospheric pressure; such fluctuations do not negatively effect the operation of the reactor assemblies. Thus, for example, in some embodiments, the reactor assembly is enclosed in a pressurized flexible dome structure similar to those used, for example, for covering sports stadiums under positive pressure. Such pressure differentials from atmospheric do not significantly influence the operation of the claimed reactor assemblies and the methods of the invention, since such differences are minor when compared to the hydrostatic pressure imparted by the liquid column disposed within the addition tube.

The hydrolysis zone is not limited to a particular shape or volume. In some embodiments, the hydrolysis zone is overall of a cylindrical shape, with inner diameter of the hydrolysis zone being equal to or greater than the inner diameter of the addition tube. In embodiments, the volume of the hydrolysis zone is in the range from about 20 to 200 m$^3$. The hydrolysis zone is optionally constructed to include areas of vertical and horizontal flow of the movement of biomass slurry, for example, by including suitable pipe adapters that allow for turning flow at a desired angle (e.g. 90 or 180 degrees, and a suitable pipe channel with optional mixers). Such optional embodiments permit installation of additional volume capacity to the hydrolysis zone, thereby increasing residence time of the slurry in the hydrolysis zone.

In embodiments, a mixer assembly is disposed with in the addition tube, the discharge tube, or both. The mixer assembly comprises a mixing shaft, mixing blades, and a motor to drive the mixing shaft. In embodiments, the mixer assembly or the mixing shaft is substantially annular. In embodiments, the mixer shaft is constructed from shaft sections connected using pipe connectors similar to or the same as those used in the drilling industry for making water, oil or natural gas wells. For example, a drilling rig derrick mounted on top of the reactor assembly and substantially over the end of the addition tube distal to the hydrolysis zone can be conveniently used to facilitate installation or retrieval the mixer shaft with any blades for service or cleaning. Various bearings known in the art can be mounted inside the reactor assembly and can be optionally used to fix the position of the mixing shaft in order to achieve a more stable and smooth non-wobbling operation thereof.

Methods and Materials

The biomass employed to form the biomass slurries include an amount of pentose compounds. Prior to contacting a reactor assembly of the invention, the pentose compounds present in the biomass comprise polymeric species such as pentosanes and hemicelluloses. For the purposes of obtaining industrially attractive amounts and yields of pentose compounds, a pentosane-containing biomass is employed having a pentosane content of about 10 wt % to 30 wt %, or about 15 wt % to 30 wt % pentose content based on dry biomass. Non-limiting examples of pentosane-containing biomass include: cereal straw such as straw of wheat, rye, oat, rice, barley, hulls and husks from processing of cereal grains such as oat, rice, barley, cottonseed, oil palm trunks, oil palm fronds, oil palm empty fruit bunches, palm nut shells, corn stover, corn cobs, corn fibers, sugar cane bagasse, hardwood and hardwood saw dust, cuttings and shavings, cereal bran, tree and shrub leafs, guayule biomass resides from rubber extraction, tree and ground nut shells, such as shells of walnut, pecan, pistachios, almond, hazelnut, peanuts, and other nuts, olive pits and residues from oil extraction, pits and pit shells from pit fruits such as cherry, apricots, plums and peaches, banana peels and biomass, artichoke plant biomass, safflower plant biomass, broccoli and cauliflower residues, miscanthus, milkweed, switch grass and other various grasses and hay.

One or more types of pentosane-containing biomass are employed to form the biomass slurries applied to one or more reactor assemblies of the invention. Such types of biomass include, in various embodiments, different parts of the same species of plants (e.g. oil palm trunks, fronds and empty fruit branches), and/or biomass from different species of plants, for example, wheat straw, rye straw, barley stray, oat straw, sorghum straw, or sugar cane bagasse blended with eucalyptus wood chips or saw dust. Different types of the biomass can also be used as seasonal alternatives feedstocks, depending on local availability.

Soluble pentose compounds obtained using the methods of the invention are formed in the reactor assemblies of the invention by hydrolysis of glycosidic bonds of pentosanes, elimination reactions, or by incidental oxidation reactions that may occur due to presence of air in the biomass particles. The soluble pentose compounds are present in the liquid hydrolysate obtained after separation thereof from hydrolyzed biomass solids as described above in relation to the reactor assemblies. The liquid hydrolysate can contain various other compounds such as organic and inorganic salts comprising elements such potassium, sodium, calcium, magnesium, iron, phosphate, ammonia, sulfate, chloride and other elements that are associated with biomass. In some embodiments, liquid hydrolysates further contain an amount of soluble lignin compounds. In some embodiments, liquid hydrolysates further contain an amounts of hexose compounds, including glucose associated with various forms of starch and cellulose. Depending on the severity of operational conditions such as acidity, temperature and residence time within the hydrolysis zone of a reactor assembly of the invention, and further depending on the type of biomass used within a reactor assembly, hexose content in the liquid hydrolysate can vary from trace amounts to an amount greater than the amount of pentoses obtained in the same liquid hydrolysate.

In embodiments, in order to achieve a uniform flow of biomass slurry through the various outlets, valves etc. of the reactor assembly, biomass solids are prepared for slurry formation by sizing. Sizing includes any method for reducing the average size of discrete particles or pieces of the biomass. For example, raw biomass is suitably chopped, milled, cut, shredded, screened, and the like to yield discrete particles or pieces suitable to maintain movement of a biomass slurry formed from the sized biomass through a reactor assembly. Some biomass sources, such as cereal hulls, nut shells and bran particles can be used in "as is" forms without any additional milling, sizing or cutting. Cereal straw can be cut using straw choppers known in the art. Tree and shrub limbs, oil palm fronds and trunks can be shredded and/or milled to form chips or fragments of size permissive to form a biomass slurry that moves through the reactor assemblies as shown without impedance due to large size pieces of biomass getting stuck within the structures of the reactor assemblies that are contacted by the biomass slurry. In some embodiments, sizing of the biomass particles or pieces is carried out to provide biomass particles or pieces having at least one dimension of less than about 10 centimeters, and in some embodiments, not to exceed about 5 centimeters, and in some embodiments not to exceed about 1 centimeter. Non-limiting examples of suitable biomass particles can be in a form of milled flour, saw dust and the like. Biomass fragments that contain some amounts of dust particles can optionally be sprayed with a liquid, such as water in order to suppress dust formation.

To the great advantage of industrial practice, elaborate, costly and vulnerable to rapid abrasive wear devices known in the art for delivery of the biomass solids against pressure of the headspace in hydrolysis reactors known in the art are not required for practicing the present invention. Pressurized means of delivery of the biomass solids include but are not limited to centrifugal pumps and other pumps with pressure locks, pressurized auger and screw devices, and the like. The reactor assemblies and methods of the invention require no pressurized means of delivery of biomass solids. The biomass addition tube is open to atmospheric or ambient pressure at the top thereof, that is, at the end of the tube distal from the hydrolysis zone. Thus the biomass solids are simply delivered to the addition tube or mixing zone of the reactor assemblies of the invention by one or more means known in the art for conveyance of solids at ambient or atmospheric pressure, such as industrial means for vertical conveyance of solids including conveyor belt assemblies, simple (unpressurized) auger or screw conveyors, bucket elevators, and the like. Suitable conveyance means include those employed in the industry for lifting and unloading agricultural products such as grains, wood products, waste biomass, or mining materials. The biomass solids are applied at a selected rate and at ambient pressure to the mixing zone at the top of the biomass addition tube via the addition port. In embodiments, the biomass solids are applied to the mixing zone of a reactor assembly in buckets or containers using muscular propulsion derived from renewable energy of animal feed, such as by using beasts of burden ascending to a location proximal to the addition port or mixing zone of the reactor assembly via a spiral walkway.

The biomass slurry applied to the addition tube of a reactor assembly of the invention comprises, consists essentially of, or consists of an admixture of biomass solids and an aqueous liquid. The slurry includes at least about 1 wt % biomass solids and as much as about 50 wt % biomass solids; in embodiments the slurry includes about 5 wt % to 25 wt % biomass solids or about 10 wt % to 15 wt % biomass solids.

In some embodiments, the aqueous liquid consists essentially of water, wherein minor (less than 3 vol %), trace (less than 1 vol %) or other incidental quantities of water miscible solvents arise during microbial processes ongoing within the biomass solids during harvest, storage, sizing, transportation, delivery and applying of the biomass solids to a reactor assembly. Such biologically arising water miscible solvents are dissolved by the aqueous liquid during slurry mixing and/or hydrolysis and are thus incorporated in the aqueous liquid.

The aqueous liquid is mixed with biomass solids in the biomass mixing zone situated operably at the top of the addition tube of the reactor assemblies of the invention to yield a biomass slurry. The mixing is advantageously carried out at atmospheric pressure. In some embodiments, the aqueous liquid is heated prior to mixing with biomass solids. In some such embodiments, the aqueous liquid is added to the biomass at or near the boiling temperature of the aqueous liquid at atmospheric pressure. Where the aqueous liquid consists essentially of or consists of water, slurry formation is suitably carried out by adding the water at a temperature of about 20° C. to 99° C. to the biomass solids. In some embodiments a heated aqueous liquid is added in the mixing zone to biomass solids at ambient temperature. In some such embodiments, the temperature of the resulting slurry is targeted to be about 70° C. to 95° C.

The aqueous liquid in the claimed process is added to one or more biomass solids in the mixing zone of the reactor assemblies to form a biomass slurry. On a dry basis, undissolved biomass solids account from about 1 wt % to about 20 wt % of the weight of the slurry. In embodiments, the amount of the undissolved biomass solids entering hydrolysis zone is about 5 wt % to 10 wt % based on dry biomass.

In carrying out the hydrolysis of pentosane-containing biomass, the pH of the liquid phase of the biomass slurry is advantageously adjusted to be in the range between about 1.5 and 6.0 when measured at 25° C., as such pH results in optimal rate of hydrolysis and yield of pentose compounds. In some embodiments the pH at 25° C. is adjusted to be about 1.5 to 5.5, or about 1.5 to 5.0, or about 1.5 to 4.8, or about 1.5 to 4.5, or about 2.0 to 5.0, or about 2.0 to 4.8. The pH values are selected in some embodiments depending on the material of construction, to minimize corrosion of the reactor parts, and to minimize or completely abate formation of undesired decomposition products arising from pentoses and hexoses, such as furfural and hydroxylmethylfurfural.

Some forms of pentosane-containing biomass become acidic during hydrolytic treatments in pure water. Acidification of such biomass is caused by hydrolysis of carboxylate ester groups present in the biomass polysaccharides, yielding the corresponding carboxylic acid species. In some embodiments, a source of carboxylic acid generated by the hydrolysis is acetate ester groups present in the biomass, which hydrolyze to form acetic acid. During hydrolytic treatment of a pentosane-containing biomass by means of elevated temperature and pressure, some acetate groups hydrolyze regardless of the pH of the hydrolysis liquid used, thereby forming acetic acid which effects a pH shift toward acidic values. Further, if air or another source of oxygen is not sufficiently excluded during hydrolysis, aldehyde groups present on the reducing sugars present in the biomass contribute to the formation of carboxylic species in the form of aldonic acids. Still further, moist cellulosic biomass is subject to chemical changes due to metabolic action of incidental microbial flora resulting in the formation of various carboxylic acids (for example, lactic acid, butyric acid, or tricarboxylic cycle compounds).

We have found that using the methods of the invention to hydrolyze pentosane-containing biomass, the acidity levels arising from the above mentioned sources are sufficient to provide accelerated hydrolysis rates, increased yield of pentose compounds in the liquid hydrolysate obtained, or both. The methods of the invention are suitably conducted without undue adjustments of pH due to innate ability of the hydrolyzed biomass to produce sufficient carboxylic acids upon hydrolytic treatment. While no pH adjustment by addition of acids or bases is required to efficiently carry out the methods of the invention, it is possible to adjust the pH of the biomass slurry applied to a reactor assembly, if desired, by addition of one or more acid or base species in order to further accelerate hydrolysis or yield of pentose compounds in the resulting liquid hydrolysate. Agents to adjust pH are optionally added to a biomass source during mixing of the biomass slurry, such as by addition of the pH adjusting agent to the water or an aqueous liquid mixed with the biomass to form the slurry; or during movement of the biomass slurry into or through the mixing zone, into or through the addition tube, or within the hydrolysis zone of one or more reactor assemblies of the invention.

Examples of acids that are optionally employed to adjust pH of the biomass slurry prior to, during, or even after applying the slurry to a reactor assembly of the invention include phosphoric acid, alkali metal dihydrogen phosphate, ammonia dihydrogen phosphate, sodium hydrogen sulfate, potassium hydrogen sulfate, nitric acid, hydrochloric acid, sulfuric acid, sulfonic acids, lactic acid, citric acid, succinic acid, oxalic acid, and the like as well as combinations thereof.

Once applied to the addition tube of a reactory assembly of the invention, the biomass slurry proceeds downward in the addition tube, aided by gravity and optionally by the one or more mixer blades present and providing mixing within the addition tube. The hydrolysis zone operates at elevated temperatures and pressures in order to achieve effective hydrolysis and dissolution of the resulting pentose compounds. In some embodiments, heat is applied to the biomass slurry present within the addition tube. In some embodiments, heat is applied to the biomass slurry present in the hydrolysis zone. In some embodiments, heat is applied to the biomass slurry both within the addition tube and within the hydrolysis zone. The one or more heat sources employed within the reactor assemblies provide a target temperature within the hydrolysis zone of about 100° C. to 180° C., for example about 110° C. to 180° C., or about 120° C. to 180° C., or about 130° C. to 180° C., or about 140° C. to 180° C., or about 150° C. to 180° C., or about 160° C. to 180° C., or about 130° C. to 175° C., or about 130° C. to 170° C., or about 130° C. to 165° C., or about 130° C. to 160° C., or about 140° C. to 170° C., or about 150° C. to 170° C., or about 150° C. to 165° C., further as selected by the operator for safety, convenience, and/or for optimizing the methods and reactor assemblies of the invention for maximum hydrolysis rate, yield of pentose compounds, or both. When the hydrolysis zone is operated at temperatures of about 150° C. to 160° C. and without addition of mineral acids, formation of undesired decomposition products arising from pentoses and hexoses, such as furfural and hydroxymethylfurfural is minimized, and lignin dissolution is further minimized.

Application of heat to the hydrolysis zone is necessary to achieve the selected operational temperature therein. The source of heat is any of a variety of such sources known in the art, for example heat exchangers, steam injection, heating jackets, and the like. In embodiments, steam injection is also useful to maintain the biomass slurry in an agitated state within the reactor assembly, reducing or avoiding potential clogging of the channels by the biomass solids. The heat source is applied at least to the hydrolysis zone; in embodiments heat is also applied to the addition tube. In some embodiments, the aqueous liquid added to the biomass solids in the mixing zone is heated such that the resulting slurry is elevated in temperature over ambient temperatures at the point the slurry is applied to the addition tube.

In embodiments, one or more portions or zones of reactor assembly containing heated biomass slurry are insulated to maintain a targeted temperature and/or minimize heat losses. The temperature values at any given location within the reactor assembly may fluctuate considerably, and deviate temporarily from the intended operational temperatures for example, within 5° C. to 10° C., due to uneven heat transfer between heat transferring surfaces, locations of steam injection ports and timing of their operation, agitation rates and shapes of agitation paddles or blades. The values specified herein for operational temperatures represent average values.

The hydrostatic pressure within the hydrolysis zone is maintained in the range of about 2 bars to 10 bars, or about 3 bars to 10 bars, or about 4 bars to 10 bars, or about 5 bars to 10 bars, or about 2 bars to 9 bars, or about 2 bars to 8 bars, or about 2 bars to 7 bars, or about 2 bars to 6 bars, or about 2 bars to 5 bars, or about 2 bars to 4 bars, or about 3 bars to 9 bars, or about 4 bars to 8 bars, or about 5 bars to 7 bars. In all embodiments the reactor assembly is configured to provide hydrostatic pressure to the hydrolysis zone in excess of the pressure of saturated steam at the intended operational temperature in the hydrolysis zone. No external source of pressurization is required to achieve the recited pressures within the hydrolysis zone: that is, no source of pressure other than hydrostatic pressure is employed to operate the reactor assembly. The height of the liquid column in the biomass addition tube varies with usable height of the addition tube, or due to fluctuation in the liquid level within the addition tube. In order to reduce or eliminate boiling, steam formation, cavitation of the biomass slurry in the hydrolysis zone, and other operating issues, the operating temperature of the hydrolysis zone is maintained somewhat below the boiling point of the aqueous liquid or liquid hydrolysate within the hydrolysis zone, for example about 1° C. to 10° C. below the boiling point the liquid contents of the hydrolysis zone.

Exemplary design considerations involved in providing a reactor assembly having these advantageous properties are easily envisioned by one of skill. For example, where the aqueous liquid consists of water, a targeted hydrolysis zone temperature of 160° C. requires hydrostatic pressure of 5 bars to 6 bars, for example 5.17 bars, to maintain water in the liquid form within the hydrolysis zone. One bar is typically equal to 0.9869 atmospheres or 14.504 psi. In order to provide the required pressure solely by hydrostatic means employing the liquid column present in the addition tube, the height of the liquid column in the addition tube must be at least about 53 meters.

Residence time of the biomass slurry within the hydrolysis zone is controlled by the dimensions of the reactor assembly as designed as well as the rates of addition and removal of mass therefrom. Within a single reactor assembly, residence time is controlled via the competing rates of the addition of fresh biomass slurry and withdrawal of hydrolyzed biomass slurry. The residence time of the biomass slurry in the hydrolysis zone is advantageously controlled to be about 5 minutes to 3 hours, for example about 5 minutes to 2.5 hours, or about 5 minutes to 2 hours, or about 5 minutes to 1 hour, or about 10 minutes to 3 hours, or about 15 minutes to 3 hours, or about 30 minutes to 3 hours, or about 1 hour to 3 hours, or about 10 minutes to 2 hours, or about 15 minutes to 1 hour.

After the period of residence in the hydrolysis zone of a reactor assembly, the biomass slurry is converted to hydrolyzed biomass slurry. The discharge of hydrolyzed biomass slurry is conducted via a discharge device, which is a discharge tube or discharge valve as described above. Where employed, the discharge valve is located substantially on or proximal to a bottom area of the hydrolysis zone. Examples of such valves are well known in the art. For example, piston valves or ball valves or butterfly valves are useful as discharge valves for the reactor assemblies of the invention. In embodiments, the decrease in pressure incurred by opening the discharge valve can be quite rapid and may lead to boiling of the aqueous liquid within the hydrolysis zone, or even a steam explosion within biomass particles and evaporation of some liquid as a steam comprising water and some acetic acid vapors. In such embodiments, the release of the slurry is performed into a containment or a tank allowing the steam to escape, for example through a heat exchanger or condenser. The resulting condensate can be recycled as it is useful as the aqueous liquid or a portion thereof for making the biomass slurry, or for subsequent washing of hydrolyzed biomass solids prior to a final hydrolyzed biomass solids dewatering step.

In the embodiments shown e.g. in FIGS. 2 and 3, a discharge tube in fluid communication with the hydrolysis zone provides an ascending flow to withdraw hydrolyzed biomass slurry from the hydrolysis zone. The ascending flow further controls the residence time in the hydrolysis zone by controlling the rate of removal of hydrolyzed biomass slurry. The discharge tube acts as a communicating vessel with the descending flow of the addition tube and the mass within the hydrolysis zone to provide the resulting residence time in the hydrolysis zone.

In embodiments of the reactor assemblies comprising a discharge tube, the flow of the biomass slurry through a reactor assembly of the invention is facilitated by addition of biomass slurry from the addition tube and withdrawal of the hydrolyzed biomass slurry via the discharge tube. In some embodiments, a headspace is allowed to form or is imposed on top of the liquid level in the discharge tube. In such embodiments, the pressure of within the headspace is allowed to equilibrate to atmospheric or ambient pressure, by allowing any steam arising from boiling of the slurry in the withdrawal channel to escape through a heat exchanger or condenser. The openings of such heat exchangers or condensers for escaping steam can be optionally connected to one or more devices for controlling composition and amount of escaping steam and capturing any incidental volatile organic compounds present in the vapor phase (e.g. acetic acid) via suitable gas washing or scrubbing equipment known in the art.

In some embodiments of the reactor assemblies comprising a discharge tube, the heat of the hydrolyzed biomass slurry within the discharge tube is recaptured by means of heat exchanger jackets employed to add heat to the biomass slurry in the addition tube. In some embodiments of the reactor assemblies comprising a discharge tube, the addition tube is located inside of the discharge tube, or vice versa. Such an arrangement provides for effective heat transfer between two flows of the slurry in opposite directions, thereby providing for energy savings.

In embodiments, the reactor assemblies of the invention include a discharge valve at or near the bottom of the hydrolysis zone for intermittent or periodic purging of the assembly from accumulated sediment, sand or otherwise undesirable or stray objects that can enter the addition tube with the biomass slurry. Accumulation of sufficient sediment for performing a purging procedure, can be, for example, observed through an observation window in the appropriate area of hydrolysis section of the reactor, or by an optical sensor or camera inside the reactor. Such use of the discharge valve reduces or eliminates the need for dedicated washing step of biomass solids prior to forming or applying a slurry thereof to the reactor assembly. Such use of the discharge valve also reduces or eliminates the need for dedicated downtime of the reactor assembly for washing or dislodging of objects from the hydrolysis zone.

In some embodiments, the hydrolyzed biomass slurry that forms in the hydrolysis zone is removed and then separated into hydrolyzed biomass solids and a liquid hydrolysate by one or more dewatering modules as described above. In some such embodiments, a portion of the liquid hydrolysate is returned or recycled to the reactor assembly. The recycled portion of the liquid hydrolysate is thus applied as the aqueous liquid or a portion thereof used to form biomass slurry from fresh biomass solids applied to the mixing zone. The partition and recycling of liquid hydrolysate contributes to a continuous process wherein a liquid hydrolysate with higher titers of pentose compounds is obtained than would be so obtained from a single cycling of aqueous liquid used to obtain liquid hydrolysate. The ability to provide higher concentrations of pentose compounds minimizes the need to distill large amounts of water and rely on complex evaporators involving two or more evaporative stages in order to obtain dried pentose compounds as a final product of the methods of the invention.

The liquid hydrolysate that results from a single cycle of aqueous liquid used to obtain liquid hydrolysate by employing the methods and reactor assemblies of the invention includes about 0.1 wt % to 15 wt % pentose compounds, for example about 0.1 wt % to 12 wt %, or about 0.1 wt % to 10 wt %, or about 0.1 wt % to 8 wt %, or about 0.1 wt % to 6 wt %, or about 0.1 wt % to 4 wt %, or about 0.1 wt % to 2 wt %, or about 0.5 wt % to 15 wt %, or about 1 wt % to 15 wt %, or about 2 wt % to 15 wt %, or about 5 wt % to 15 wt %, or about 10 wt % to 15 wt %, or about 1 wt % to 10 wt %, or about 1 wt % to 5 wt %, or about 1 wt % to 2 wt % pentose compounds. In embodiments, the concentration of pentose compounds in the recycled hydrolysis liquid applied to the hydrolysis zone is maintained in the range of concentrations from about 2 wt % to about 20 wt % pentose compounds, or about 2 wt % to 15 wt %, or about 2 wt % to 12 wt %, or about 2 wt % to 10 wt %, or about 3 wt % to 20 wt %, or about 4 wt % to 20 wt %, or about 5 wt % to 20 wt %, or about 8 wt % to 20 wt %, or about 3 wt % to 15 wt %, or about 4 wt % to 12 wt %, or about 5 wt % to 10 wt %, or about 8 wt % to 12 wt %, or about 8 wt % to 10 wt % pentose compounds.

As described above, a portion of the liquid hydrolysate may be recycled for making fresh biomass slurry. In some embodiments, a first portion or the entirety of the liquid hydrolysate is harvested, while optionally a second portion is recycled. Harvested liquid hydrolysate is further processed to provide dry pentosane compounds, for example by evaporation of a part of the remaining water or aqueous liquid to provide a shippable and storable liquid hydrolysate concentrate with content of the desired pentose compounds ranging from about 30 wt % to about 70 wt %, or about 40 wt % to 70 wt %, or about 50 wt % to 70 wt %, or about 60 wt % to 70 wt %, or about 30 wt % to 60 wt %, or about 30 wt % to 50 wt %, or about 30 wt % to 40 wt %. In embodiments where the liquid hydrolysate comprises at least about 10 wt % pentose compounds, concentration of the liquid hydrolysate to the concentrate can be accomplished using a single stage falling film or a wiped film evaporator.

During initial startup for continuous or semi-continuous or batch operation of a reactor assembly of the invention, an aqueous liquid (with or without pH adjustment) is suitably used, or alternatively a recycled liquid hydrolysate from prior operations of the same or similar reactor assembly or similar hydrolysis process is used, or a combination of aqueous liquid and recycled liquid hydrolysate is used for initial hydrolysis of biomass in the reactor assembly hydrolysis zone. In embodiments, hexoses and soluble hexose oligomers and polymers are also present in the (recycled) liquid hydrolysate, as most types of agricultural and forestry cellulosic biomass contain some quantities of readily hydrolysable hexose polysaccharides such as starch or hexose fragments of hemicellulose polymers or even some degraded or oxidized soluble fragments of cellulose.

In some embodiments, the hydrolyzed biomass slurry that forms in the hydrolysis zone is removed and then separated into hydrolyzed biomass solids and a liquid hydrolysate by one or more dewatering modules as described above, further wherein the hydrolyzed biomass solids are subjected to a washing step with water or a condensate produced in the process, to minimize retention of the desired solubilized pentose compounds by the porous hydrolyzed biomass solids. In some such embodiments the washed hydrolyzed biomass solids are further subjected to a second dewatering step. The resulting dewatered hydrolyzed biomass can be further dried in a drum drier, kiln or tumble drier, to minimize moisture content, for example using a low grade heat of a hot air heated by the low pressure steam or condensate produced elsewhere in the process. The resulting dry hydrolyzed biomass can be used as a primary energy source (hog fuel) for steam generation and other energy or heat requirements for carrying out the methods of the invention, or can be used in a variety of other ways known in the art.

The liquid hydrolysate obtained in the process is useful as a cost-effective and sustainable starting material for industrial production of a plethora of important chemical products known in the art, such as furfural, furfuryl alcohol, levulinic acid and its esters, furan and tetrahydrofuran, tetrahydrofurfuryl alcohol, polytetramethylene ether glycol, food grade xylose, technical and food grade xylitol, 1,4-anhydroxylitol, as well as the ketals of 1,4-anhydroxylitol with levulinic esters (which are useful as monomers in making high performance impact resistant renewable thermoplastics known in the art).

Depending on the severity of operational conditions of the hydrolysis (e.g. residence time in the hydrolysis zone, operational temperature and pH), the resulting hydrolyzate can comprise dissolved pentose compounds predominantly in the form of soluble xylose oligomers or in the form of xylose monosaccharide, while incidental quantities of hexoses are present predominantly as monosaccharides. The pentosane solubilization and depolymerization at the conditions of the disclosed process has considerable selectivity over cellulose and lignin. With operations using lower pH conditions of the specified ranges, and with higher temperatures of the specified ranges, some quantities of soluble hexose monosaccharides and polysaccharides arising from cellulose, as well as minor quantities of soluble lignin compounds will be also present in the liquid hydrolysate in addition to the pentose compounds.

In some embodiments wherein oligomers of xylose are a predominant form of pentose compounds present in the liquid hydrolysate, the liquid hydrolysate is further treated with microorganisms capable of consuming hexoses while leaving pentoses in predominantly unchanged form. For example, the liquid hydrolysate can be fermented with baker's yeast, *Saccharomyces cerevisiae*, or with other yeast species capable of fermenting hexoses to form ethanol. After the fermentation, the treated hydrolysate comprising xylose oligomers is purified to remove yeast cells and other solid debris associated with fermentation, salts, and color bodies using by methods known in the art. In some such embodiments the treated hydrolysate is subjected to an additional hydrolysis employing a mild acid catalyst or an enzyme, such as one or more xylanases known in the art, thereby resulting in a solution of xylose of improved purity.

In some embodiments wherein xylose monosaccharide is a major or prediminant form of soluble pentose compounds (with incidental quantities of hexoses present as monosaccharides or as soluble polysaccharides, such as starch oligomers) in the liquid hydrolysate, the liquid hydrolysate is further treated with microorganisms capable of consuming hexoses while leaving pentoses in either predominantly unchanged form and/or in a reduced form such as xylitol or arabitol. For example, the liquid hydrolysate can be fermented with the baker's yeast, *Saccharomyces cerevisiae*, or with other yeast species capable of fermenting hexoses to ethanol. After the fermentation, the treated hydrolysate comprising is purified to remove yeast cells and other solid debris associated with fermentation, salts, and color bodies using by methods known in the art.

The liquid hydrolysates, treated hydrolysates, and concentrates thereof comprising soluble pentose compounds and optional incidental quantities of hexose compounds are particularly attractive and suitable for use as animal feed because of the mild conditions of hydrolysis, absence of strong acids and of undesired decomposition products such as furfural and hydroxymethylfurfural or large quantities of soluble lignin compounds. The resulting lignocellulosic residue, with or without dewatering, and with or without separating the pentose-containing hydrolysate therefrom, is also particularly attractive as a major component of animal feed due to improved digestability of remaining insoluble cellulose and due to the absence of hydrolysis byproducts that can detract animals from adequate consumption of a fibrous feed. In particular, in arid agricultural areas with limited water supplies and with significant availability of orchard biomass (e.g. woody tree pruning, whole trees from scheduled orchard replacements or principal by-products of nut shelling operations), the pentose hydrolysate and the insoluble cellulosic residue separated therefrom can reliably serve as a quality fiber feed for dairy production.

Among applications for the remainder of hydrolyzed biomass solids generated in the process include feedstocks for energy generation (as a boiler or gasifier feed). Agriculturally useful ash-contributing mineral nutrient elements from the hydrolyzed biomass solids become dissolved in the pentose compound syrup, thereby providing for a consolidated recovery of and reuse of such compounds in a usable form as crop nutrients. Given the energy content residing in the lignin and non-hydrolyzed cellulosic polymers of hydrolyzed biomass solids, the entire process of disclosed herein is essentially self-sufficient in meeting its energy needs for operation. The process results in a convenient shippable liquid pentose compounds syrup suitable for further consolidation and processing to various value-added industrial and food products.

The reactor assemblies and methods disclosed herein are further useful for a sequential treatment of biomass solids, wherein hydrolyzed biomass solids having depleted pentosane content are subsequently treated again using the same or a similar process and reactor assembly. In such retreatment methods, the aqueous liquid is adjusted to have a pH of about 1 to 3, such as about 1.5 to 2.5. The resulting liquid hydrolysate of such retreatment methods contain predominantly products of hydrolysis of cellulose (glucose), with a minor content of pentose compounds. Such liquid retreatment hydrolysates are suitable for fermentative production of ethanol or other organic chemicals.

The invention illustratively disclosed herein can be suitably practiced in the absence of any element which is not specifically disclosed herein. Additionally each and every embodiment of the invention, as described herein, is intended to be used either alone or in combination with any other embodiment described herein as well as modifications, equivalents, and alternatives thereof. In various embodiments, the invention suitably comprises, consists essentially of, or consists of the elements described herein and claimed according to the claims. It will be recognized that various modifications and changes may be made without following the example embodiments and applications illustrated and described herein, and without departing from the scope of the claims.

The invention claimed is:

1. A process for making soluble pentose compounds from biomass comprising pentose polymers in a reactor assembly, the process comprising:

a) forming a biomass slurry in a biomass mixing zone of the reactor assembly at an atmospheric pressure by mixing biomass with an aqueous liquid, wherein the temperature of the aqueous liquid in the slurry is maintained at or below the boiling point thereof at atmospheric pressure;

b) transferring the slurry downward from the mixing zone to a hydrostatically pressurized hydrolysis zone by a gravity flow through an addition tube, the addition tube providing a continuous liquid contact between the mixing zone and a hydrolysis zone at the bottom of the addition tube, wherein the transfer of the slurry is provided by the hydrostatic pressure due to the height of the slurry in the addition zone that exceeds the hydrostatic pressure provided by the remainder of the slurry contained in the reactor assembly;

c) heating the slurry to achieve and maintain an operational temperature of about 120° C. to 180° C. in the hydrostatically pressurized hydrolysis zone, wherein a pH of the aqueous liquid in the hydrolysis zone is about 2 to 4.8, as measured at 25° C.;

d) maintaining a slurry level in the addition zone to provide a hydrostatic pressure in the hydrolysis zone in excess of the vapor pressure of the aqueous liquid at the operational temperature of the hydrolysis zone, e) withdrawing slurry though a discharge valve connected to the hydrolysis zone, or from above the hydrolysis zone via a discharge tube connected to the hydrolysis zone, wherein entry of slurry to the discharge valve or discharge tube takes place at a positive hydrostatic pressure of the slurry or at atmospheric pressure, thereby providing a hydrolyzed biomass slurry comprising biomass solids and a liquid hydrolysate, the hydrolyzed biomass slurry having reduced content of pentosanes and the liquid hydrolysate having increased content of soluble pentose compounds, as compared to the composition of biomass and aqueous liquid in the slurry formed in the mixing zone.

2. The process of claim 1 further comprising separating the hydrolyzed biomass solids from liquid hydrolysate.

3. The process of claim 2 wherein a portion of separated liquid hydrolysate is mixed with fresh biomass in the mixing zone or with biomass slurry in the addition tube.

4. The process of claims 3 wherein the hydrolyzed biomass solids are subjected to an aqueous washing step, wherein the liquid resulting from the washing step is mixed with biomass in the biomass mixing zone or is added to the addition tube.

5. The process of claim 1, wherein the biomass slurry entering the hydrolysis zone comprises about 4 wt % to 12 wt % soluble pentose compounds.

6. The process of claims 5, wherein the liquid hydrolysate is further treated with yeast, wherein the treatment with yeast results in one or more effects on the composition of the liquid hydrolysate, said effects selected from a group of consisting of: (a) removal of soluble hexose compounds, (b) reduction of xylose to xylitol, or (c) production of ethanol.

* * * * *